United States Patent [19]

Fourie et al.

[11] Patent Number: 5,137,908
[45] Date of Patent: Aug. 11, 1992

[54] 4-AZAHEXACYCLODODECANE COMPOUNDS

[75] Inventors: Theunis G. Fourie; Friedrich O. Snyckers, both of Pretoria, South Africa

[73] Assignee: Noristan Holdings Limited, Pretoria, South Africa

[21] Appl. No.: 628,512

[22] Filed: Dec. 13, 1990

[30] Foreign Application Priority Data

Dec. 13, 1989 [ZA] South Africa .................. 89/9513

[51] Int. Cl.$^5$ .................. A61K 31/40; C07D 209/56
[52] U.S. Cl. .................. 514/410; 548/417; 548/418; 548/419
[58] Field of Search .................. 548/417, 418, 419; 514/410

[56] References Cited

PUBLICATIONS

Borch, Richard F., Bernstein, Mark D., and Dupont Durst, H., *Journal of the American Chemical Society*, 1971, Jun. 16, 93(12), 2897-2904.
Sasaki, I Tadashi, Eguchi, Shoji, and Okano, Takashi., *Journal of Organic Chemistry*, 1981, 46, 4474-4477.
Sasaki, T., Eguchi, S., Kiriyama, T., and Hiroaki, O., *Tetrahedron*, 1974, 30, 2707-2712.
van der Schyf, Cornelis J., Squier, Gerald J., and Coetzee, William A., *Pharmacological Research Communications*, 1986, 18(5), 407-417.
Marchand, Alan P., Arney, Benny E. (Jr.), Dave, Paritosh R., and Satyanarayana, N., *J. Org. Chem.*, 1988, 53, 2644-2647.
van der Schyf, Cornelis J., Liebenberg, Wilna., Bornman, Riaan., Dekker, Theodor G., van Rooyen, Petrus H., Fourie, Theunis G., Matthee, Elmare., and Snyckers, Friedrich O., *S. Afr. J. Chem.*, 1989, 42(1), 46-48.

Primary Examiner—Joseph Paul Brust
Attorney, Agent, or Firm—Pennie & Edmonds

[57] ABSTRACT

4-Azahexacyclo $(5.4.1.0^{2,6}.0^{3,10}.0^{5,9}.0^{8,11})$ dodecane compounds of the formula

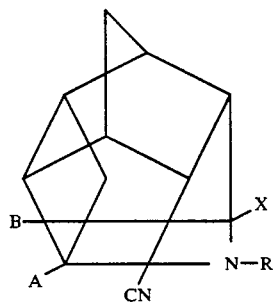

wherein R, A and B each is hydrogen; a linear or branched alkyl group having one to twelve carbon atoms and optionally including a hydroxyl or halogen substituent; or a phenyl group alone or optionally substituted with a linear or branched alkyl group having one to twelve carbons, which group optionally includes a hydroxyl or halogen substituent; and X is a hydroxyl or —NR$_2$ group where R is as stated above; or an acid addition salt of such compound. These compounds are useful in pharmaceutical compositions wherein the compound is included in an amount effective to be used as a calcium antogonist, a cardiac agent or an antihypertensive agent.

12 Claims, No Drawings

4-AZAHEXACYCLODODECANE COMPOUNDS

BACKGROUND OF THE INVENTION

This invention relates to polycyclic compounds, a process for preparing these compounds, uses and pharmaceutical compositions thereof. More particularly this invention relates to certain derivatives of 4-azahexacyclo-[5.4.1.0$^{2,6}$.0$^{3,10}$.0$^{5,9}$.0$^{8,11}$] dodecane, a process for preparing such compounds, their use as pharmaceutical agents, and pharmaceutical compositions thereof.

Subsequent to the discovery of the antiviral an anti-Parkinsonistic properties of amantadine, considerable research has taken place to exploit the medicinal properties of polycyclic compounds. U.S. Pat. No. 3,449,422 describes certain amino derivatives of pentacyclo-[5.4.0.0$^{2,6}$.0$^{3,10}$.0$^{5,9}$] undecane, such as the 8-amino derivatives (A), and their preparation as well as their activity against Asian and swine influenza viruses. In European Patent Application 82306975.2 it has been disclosed that the pentacyclo-undecane amines having structure (A) (referred to above) further-more exhibit anti-Parkinsonistic properties.

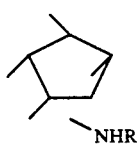

A

Antiviral properties have also been reported for a number of amino derivatives of polycyclic hydrocarbons related to A, or the so-called bird-cage type of compounds, for instance in U.S. Pat. Nos. 3,622,628; 3,536,761; 3,641,148; 3,532,741; 3,456,008 and 3,562,317.

In South African Patent 88/7542 it was demonstrated that derivatives of the amino ether (C), formed by reduction of the imino ketone (B) with sodium borohydride, exhibits useful calcium antagonistic properties. These findings, as regards the structure of the product, contradict a report by Sasaki et al. (*Tetrahedron*, 30, 2707, 1974) that under the same experimental conditions mentioned above the imino ketone is converted to the hydroxy-aza type compound (D).

Marchand et al. (*J. Org. Chem.*, 53, 2644–2647) and later van der Schyf et al. (*S. Afr. J. Chem.*, 42(1), 46, 1989) confirmed that the reduction product mentioned above was indeed the amino ether compound (C) and not hydroxy-aza compound (D). It was therefore found by the inventors of South African Patent 88/7542 that the structure of the product obtained by the reduction of compound (B) with sodium borohydride had previously been wrongly assigned by Sasaki et al.

A. P. Marchand and co-workers (*J. Org. Chem.*, 53, 2644–2647, 1988) furthermore reported that only the hydroxy-aza compound (D) was obtained by reduction of the imino ketone (B) with sodium cyanoborohydride.

In order to illustrate the aforementioned, reference is made to the reaction scheme shown immediately hereunder.

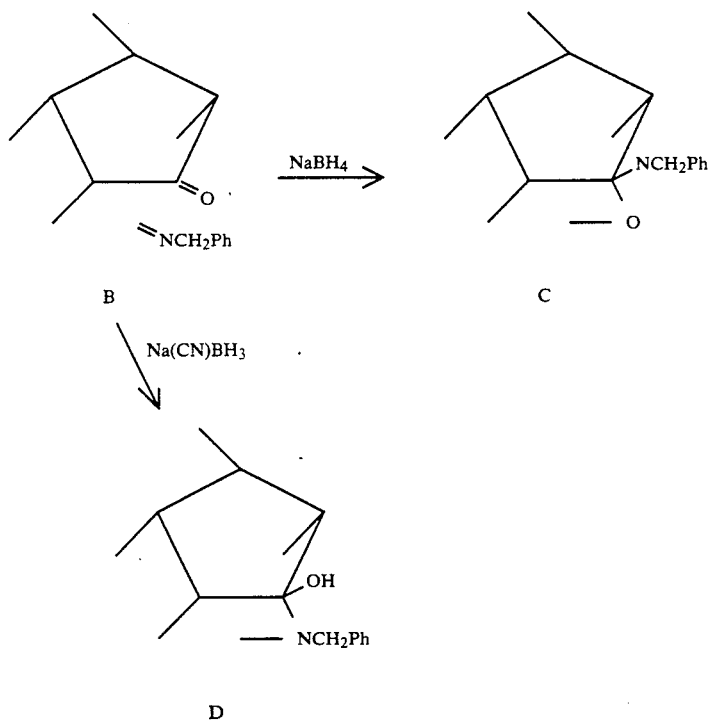

SUMMARY OF THE INVENTION

Surprisingly, however, the present inventors have recently found that reduction of imino ketone (B) with sodium cyanoborohydride, according to the procedure described by Marchand et al., not only formed the hydroxy-aza compound (D) but also certain aza nitrile compounds (E) and (F). It is reported in the literature that sodium cyanoborohydride reduces iminium ions more rapidly than carbonyl groups (R. F. Borch et al., *J. Am. Chem. Soc.*, 93, 2897, 1971; Sasaki et al., *J. Org. Chem.*, 46, 4474, 1981).

According to one aspect of the present invention, there is provided a (an alternative) process for preparing above compounds (E) and (F), the process including the step of reacting iminoketone (B) with sodium cyanide. The hydroxy aza-compound (D) referred to above, however, did not form during the aforesaid process whenever sodium cyanide was used.

The present inventors have also recently established the structure of the aza nitrile compound (E) by means of X-ray crystallographic studies. Hence neither were the structures of the abovementioned aza nitrile compounds (E and F) obtained by reaction of imino ketone with sodium cyanoborohydride or sodium cyanide, nor was their pharmacology known prior to the present invention. In order to illustrate the aforementioned, reference is made to the reaction scheme shown immediately hereunder.

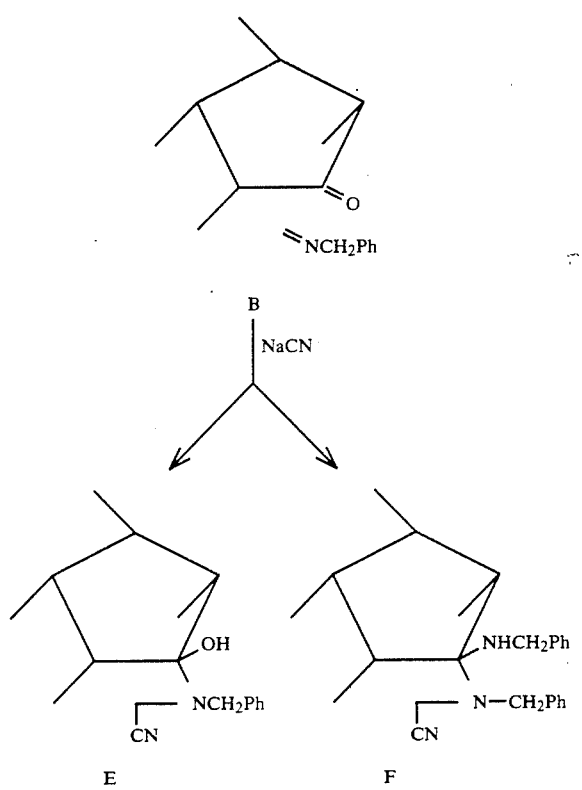

The present inventors found no calcium antagonistic activity for the hydroxy-aza compound (D) (referred to above) but to the inventors' surprise, the aza nitrile compound (E) exhibits useful calcium antagonistic properties as exemplified by several tests indicative for calcium antagonistic activity.

The calcium antagonistic property therefore seems to be associated with the cyano group, although the structure-activity relationship is not clear at this stage.

According to another aspect of the invention there are provided compounds of the general formula I:

A-R    (I)

wherein A is 4-azapentacyclo [$5.4.1.0^{2,6}.0^{3,10}.0^{5,9}.0^{8,11}$] dodecane optionally substituted with one or more substituents, preferably comprising, a cyano, an hydroxy, an amino, alkyl, aryl, nitro or keto group, and R is a substituent on the aza nitrogen, hydrogen or an unsubstituted or substituted aromatic or an unbranched or branched alkyl group, the alkyl group preferably or optionally having as a substituent an aryl or hydroxy group or halogen; and acid addition salts of such compounds.

According to a preferred aspect of the invention there are provided compounds of the general structural formula II:

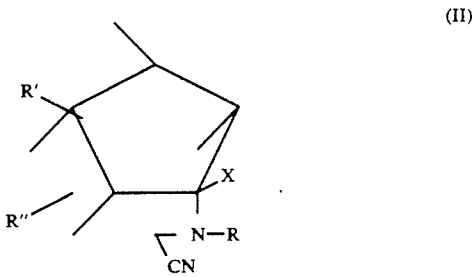

wherein R is as defined above; and R' and R" are as defined for R above; and X is an hydroxyl group or amino group; and acid addition salts of such compounds.

Preferred compounds include compounds of the general structural formulae (III):

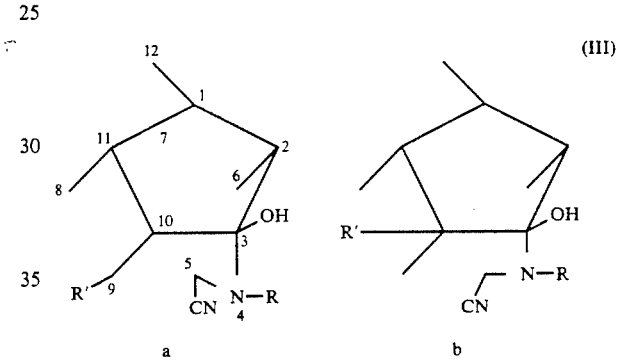

wherein R, and R' are as defined above; and acid addition salts of such compounds.

Preferred compounds of the above general formulae (III) are listed in TABLE 1 hereunder.

Compound 4 3-hydroxy-5-cyano-4-benzyl-4-azahexacyclo .[$5.4.1.0^{2,6}.0^{3,10}.0^{5,9}.0^{8,11}$] undecane, also depicted by structure E, is particularly preferred.

TABLE 1

| PREFERRED COMPOUNDS | | |
|---|---|---|
| COMPOUND NO. | R | R' |
| 1 | $CH_3$ | H |
| 2 | $(CH_2)_3CH_3$ | H |
| 3 | $(CH_2)_7CH_3$ | H |
| 4 | $CH_2C_6H_5$ | H |
| 5 | $(CH_2)_2C_6H_5$ | H |
| 6 | $(CH_2)_3C_6H_5$ | H |
| 7 | $CH_3$ | $CH_3$ |
| 8 | $(CH_2)_3CH_3$ | $CH_3$ |
| 9 | $(CH_2)_7CH_3$ | $CH_3$ |
| 10 | $CH_2C_6H_5$ | $CH_3$ |
| 11 | $(CH_2)_2C_6H_5$ | $CH_3$ |
| 12 | $(CH_2)_3C_6H_5$ | $CH_3$ |
| 13 | $CH_2CH_3$ | H |
| 14 | $(CH_2)_{11}CH_3$ | H |
| 15 | $CH_2CH(CH_3)_2$ | H |
| 16 | $(CH_2)_5CH_3$ | H |
| 17 | $C(CH_3)_2CH_2C(CH_3)_3$ | H |
| 18 | $(CH_2)_3CH_3$ | H |
| 19 | $CH_2CH_2OH$ | H |
| 20 | $C_6H_5$ | H |

The invention extends to positional and optical isomers of the abovementioned compounds.

Also according to the present invention there is provided a process for preparing the compounds of the invention as defined herein, the process including the steps of converting a parent diketone (IV) to a corresponding hydroxyamine (V) by treatment with an appropriate amine, preferably in tetrahydrofuran in the cold, followed by dehydration of a hydroxyamine (V) under mild conditions, preferable by refluxing in dry benzene, to an imino ketone (VI), which imino ketone is reduced to produce amongst other products an aza nitrile compound (III) by treatment with sodium cyanoborohydride or sodium cyanide. See reaction scheme on page 10.

In the case where R'=H, the above process may give rise to a mixture of positional isomers (IIIa and IIIb), which may be separated by any method known in the art of organic chemistry.

The compounds of the present invention have an asymmetric structure (III) and will consequently have enantiomeric forms (optical isomers).

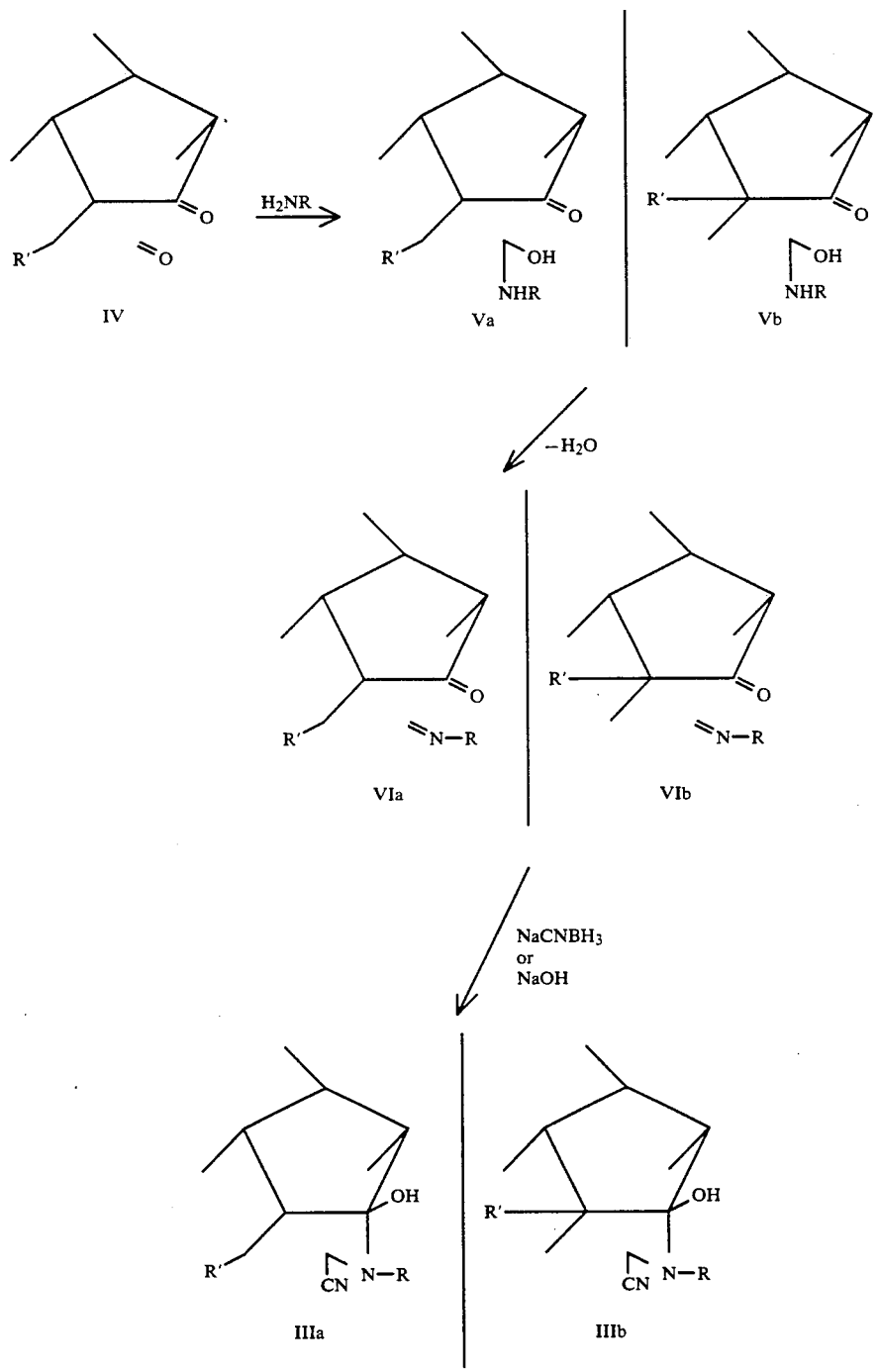

In the case where the unsubstituted diketone (IV); R'=H, which is symmetric and thus optically nonactive, is used as a starting material, the process of the invention will give rise to the formation of a racemic mixture of III; R'=H. Such enantiomers may be separated by any method known in the art of separating enantiomers. However, when R'≠H, then the parent diketone (IV; R'≠H) is in itself chiral and the process of this invention may give rise to the formation of four stereo-isomers, namely the two enantiomers of IIIa; R'≠H and the two enantiomers of IIIb; R'≠H. Whenever a pure enantiomer of IV; R'=H is used, the process will proceed with retention of chirality, i.e. a pure enantiomer of IIIa; R'≠H or IIIb; R'≠H, or a mixture thereof, will be formed. It will be understood that the ratio in which the positional isomers IIIa; R'≠H and IIIb; R'≠H are formed from compound IV; R'≠H is dependent on the reactivity of the carbonyl groups of IV; R'≠H and the steric influence of group R' and thus the reaction conditions.

Whenever a mixture of enantiomers and/or diastereomers of the compounds of this invention is produced according to the aforesaid process or any other process, such mixture may be separated into the individual components according to any method known in the art.

The invention naturally extends to compounds whenever prepared according to the process of the invention. Further details of the process according to the invention will be described in greater detail hereunder.

The compounds of the abovementioned formulae have generally shown useful calcium antagonistic properties. Accordingly, the invention extends to the use of such compounds as calcium antagonists and as calcium antagonists for cardiac conditions precipitated by uncontrolled repetitive activity and as antihypertensive compounds and to such compounds whenever used as calcium antagonists and as calcium antagonists in cardiac tissues where repetitive activity occurs, such as found during supra-ventricular tachy-arrhythmias and as antihypertensive agents. In other words the invention also extends to at least one compound of the general formulae as defined above as a calcium antagonist or when used as a calcium antagonist for cardiac conditions precipitated by uncontrolled repetitive activity or as an antihypertensive agent and when used as a calcium antagonist.

The invention further extends to calcium antagonists and/or antihypertensive compounds comprising one or more compounds of the above general formulae.

According to a further aspect of the invention there are provided pharmaceutical compositions comprising as an active ingredient, a pharmaceutically acceptable amount of at least one pharmacologically acceptable compound of the general formulae as defined above either alone or in admixture with a suitable diluent or adjuvant. The invention extends to methods of preparing such pharmaceutical compositions, and pharmaceutical compositions whenever prepared by such methods.

The invention will now be described in greater detail by means of the following non-limiting examples.

EXAMPLES

EXAMPLE 1

3-Hydroxy-5-cyano-4-benzyl-4-azahexacyclo[5.4.1.0$^{2,6}$.0$^{3,10}$.0$^{5,9}$.0$^{8,11}$] dodecane (compound 4)

To a cold, stirred solution of pentacyclo[5.4.0.0$^{2,6}$.0$^{3,10}$.0$^{5,10}$] undecan-8,11-dione (IV; R'=H) (5,0 g; 28.7 mmol) in tetrahydrofuran (100 ml) was added benzylamine (3,2 g; 30 m mol) over a period of 30 minutes. The reaction mixture was stirred, under ice-cooling, for an addition period of one hour. The resulting precipitate of the hydroxyamine V; R=CH$_2$C$_6$H$_5$; R'=H was filtered, washed with tetrahydrofuran and dried.

Compound V; R=CH$_2$C$_6$H$_5$; R'=H was refluxed in benzene (200 ml) under dehydrating conditions, e.g. a Dean-Stark apparatus, until the water of reaction had been completely removed. Evaporation of the benzene in vacuo rendered the imino ketone VI; R=CH$_2$C$_6$H$_5$; R'=H as a waxy or oily product.

The iminoketone VI; R=CH$_2$C$_6$H$_5$ was dissolved in acetic acid (15 ml) and dry methanol (250 ml). Sodium cyanoborohydride (2,0 g) was added portionwise during 5 min while stirring at room temperature for 2 h. The reaction mixture was then concentrated in vacuo, and water (100 ml) was added to the residue. The resulting suspension was stirred, and solid sodium carbonate added portionwise until evolution of carbon dioxide ceased. Excess solid sodium bicarbonate (2,0 g) was added, and the aqueous suspension extracted with chloroform (4×50 ml), dried (sodium sulphate), filtered and evaporated. A mixture of compounds 4, D and F was obtained from which 4 and F was isolated by column chromatography (silica gel). Compound 4, showed the molecular mass in the mass spectrum at m/e 290. The $^{13}$C NMR spectrum (DMSO) of compound 4 showed the following signals (ppm from TMS); 140.0, 128.3(X2), 127.7(X2), 126.3, 120.1, 106.2, 66.0, 57.0, 54.6, 49.4, 48.2, 45.6, 44.7, 42.6, 41.6, 41.4, and 41.3.

Compound F showed the molecular mass in the mass spectrum at m/e 379. The $^{13}$C NMR spectrum (DMSO) of compound F showed the following signals (ppm from TMS): 41.5, 41.7, 42.4, 43.2, 44.9, 46.0, 47.9, 48.7, 51.1, 53.2, 57.1, 68.3, 96.6, 120.2, 126.8, 127.0, 127.7, 128.2, 128.3, 128.7, 139.5, 140.5. The physical data of compound D is identical to that found by Marchand et al.

EXAMPLE 2

3-Hydroxy-5-cyano-4-benzyl-4-azahexacyclo[5.4.1.0$^{2,6}$.0$^{3,10}$.0$^{5,9}$.0$^{8,11}$] dodecane (compound 4)

To a cold, stirred solution of pentacyclo[5.4.0.0$^{2,6}$.0$^{3,10}$.0$^{5,10}$] undecan-8,11-dione (IV; R'=H) (5,0 g; 28.7 mmol) in tetrahydrofuran (100 ml) was added benzylamine (3,2 g; 30 m mol) over a period of 30 minutes. The reaction mixture was stirred, under ice-cooling, for an addition period of one hour. The resulting precipitate of the hydroxyamine V; R=CH$_2$C$_6$H$_5$; R'=H was filtered, washed with tetrahydrofuran and dried.

Compound V; R=CH$_2$C$_6$H$_5$; R'=H was refluxed in benzene (200 ml) under dehydrating conditions, e.g. a Dean-Stark apparatus, until the water of reaction had been completely removed. Evaporation of the benzene in vacuo rendered the imino ketone VI; R=CH$_2$C$_6$H$_5$; R'=H as a waxy or oily product.

The iminoketone VI; R=CH$_2$C$_6$H$_5$ was dissolved in acetic acid (15 ml) and dry methanol (250 ml). Sodium cyanide (2.0 g) was added portionwise during 5 min while stirring at room temperature for 2 h. The reaction mixture was then concentrated in vacuo, and water (100 ml) was added to the residue. The resulting suspension was stirred, and solid sodium carbonate added portionwise until evolution of carbon dioxide ceased. Excess solid sodium bicarbonate (2.0 g) was added, and the aqueous suspension extracted with chloroform (4×50 ml), dried (sodium sulphate), filtered and evaporated. A mixture of compounds 4 and F was obtained from which 4 and F was isolated by column chromatography (silica gel). It is important to note that whenever sodium cyanide was used, higher yields of compounds 4 and F were obtained. Spectroscopic data for both compounds (4 and F) were identical to those reported under Example 2.

EXAMPLE 3

3-Hydroxy-5-cyano-4-octyl-4-azahexacyclo[5.4.1.0$^{2,6}$.0$^{3,10}$.0$^{5,9}$.0$^{8,11}$] dodecane (compound 3)

To a cold, stirred solution of pentacyclo[5.4.0.0$^{2,6}$.0$^{3,10}$.0$^{5,10}$] undecan-8,11-dione (IV; R'=H) (5,0 g; 28.7 mmol) in tetrahydrofuran (100 ml) was added octylamine (3,2 g; 37 mmol) over a period of 30 minutes. The reaction mixture was stirred, under ice-cooling, for an additional period of one hour. The resulting precipitate of the hydroxyamine V; R=(CH$_2$)$_7$CH$_3$; R'=H was filtered, washed with tetrahydrofuran and dried.

Compound V; R=(CH$_2$)$_7$CH$_3$;R'=H was refluxed in benzene (200 ml) under dehydrating conditions, e.g. a Dean-Stark apparatus, until the water of reaction had been completely removed. Evaporation of the benzene in vacuo rendered the imino ketone VI; R=(CH$_2$)$_7$CH$_3$; R'=H as a waxy or oily product.

The iminoketone VI; R=(CH$_2$)$_7$CH$_3$ was dissolved in acetic acid (15 ml) and dry methanol (250 ml). Sodium cyanoborohydride (2,0 g) was added portionwise during 5 min while stirring at room temperature for 2 h. The reaction mixture was then concentrated in vacuo, and water (100 ml) was added to the residue. The resulting suspension was stirred, and solid sodium carbonate added portionwise until evolution of carbon dioxide ceased. Excess solid sodium bicarbonate (2,0 g) was added, and the aqueous suspension extracted with chloroform (4×50 ml), dried (sodium sulphate), filtered and evaporated. Compound 3 was isolated by column chromatography (silica gel). Compound 3, showed the molecular mass in the mass spectrum at m/e 312. The $^{13}$C NMR spectrum (DMSO) of compound 3 showed the following signals (ppm from TMS): 13.9, 22.0, 27.0, 28.6, 28.8, 29.4, 31.2, 41.2, 41.4, 41.5, 42.4, 44.6, 45.6, 46.1, 48.1, 54.6, 56.8, 66.2, 106.3 and 120.9.

EXAMPLE 4

3-Hydroxy-5-cyano-4-octyl-4-azahexacyclo[5.4.1.0$^{2,6}$.0$^{3,10}$.0$^{5,9}$.0$^{8,11}$] dodecane (compound 3)

To a cold, stirred solution of pentacyclo[5.4.0.0$^{2,6}$.0$^{3,10}$.0$^{5,10}$] undecan-8,11-dione (IV; R'=H) (5,0 g; 28.7 mmol) in tetrahydrofuran (100 ml) was added octylamine (3,2 g; 37 mmol) over a period of 30 minutes. The reaction mixture was stirred, under ice-cooling, for an additional period of one hour. The resulting precipitate of the hydroxyamine V; R=(CH$_2$)$_7$CH$_3$; R'=H was filtered, washed with tetrahydrofuran and dried.

Compound V; R=(CH$_2$)$_7$CH$_3$; R'=H was refluxed in benzene (200 ml) under dehydrating conditions, e.g. a Dean-Stark apparatus, until the water of reaction had been completely removed. Evaporation of the benzene in vacuo rendered the imino ketone VI; R=(CH$_2$)$_7$CH$_3$; R'=H as a waxy or oily product.

The iminoketone VI; R=(CH$_2$)$_7$CH$_3$ was dissolved in acetic acid (15 ml) and dry methanol (250 ml). Sodium cyanide (2,0 g) was added portionwise during 5 min while stirring at room temperature for 2 h. The reaction mixture was then concentrated in vacuo, and water (100 ml) was added to the residue. The resulting suspension was stirred, and solid sodium carbonate added portionwise until evolution of carbon dioxide ceased. Excess solid sodium bicarbonate (2,0 g) was added, and the aqueous suspension extracted with chloroform (4×50 ml), dried (sodium sulphate), filtered and evaporated. Compound 3 was isolated by column chromatography (silica gel). Spectroscopic data for compound 3 was identical to those reported under Example 3.

The structure of compound 3 was determined by means of X-ray crystallographic analysis according to standard procedures. The perspective drawing of 3 is shown below. The fractional coordinates are listed in Table 2.

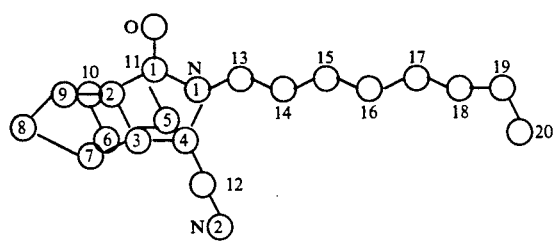

TABLE 2

Fractional coordinates (× 10$^4$) and equivalent isotropic thermal parameters (× 10$^4$ A$^{02}$) for Compound 3.

|       | X/a       | Y/b       | Z/c      | Ueq       |
|-------|-----------|-----------|----------|-----------|
| N(1)  | 320(4)    | 3214(3)   | −77(3)   | 579(7)    |
| N(2)  | −1045(6)  | 1263(4)   | −1417(4) | 1251(12)  |
| C(1)  | 2082(6)   | 3965(4)   | −225(4)  | 837(10)   |
| C(2)  | 2554(6)   | 4910(4)   | −1564(4) | 767(10)   |
| C(3)  | 1896(6)   | 4058(4)   | −2149(3) | 713(10)   |
| C(4)  | 1119(6)   | 2749(4)   | −1021(4) | 785(10    |
| C(5)  | 2951(6)   | 2101(4)   | −705(4)  | 938(11)   |
| C(6)  | 4534(7)   | 2778(5)   | −1874(4) | 1147(12)  |
| C(7)  | 3692(7)   | 3798(5)   | −2901(4) | 1036(12)  |
| C(8)  | 4964(8)   | 5090(5)   | −3317(5) | 949(13)   |
| C(9)  | 4669(6)   | 5070(5)   | −2060(4) | 922(12)   |
| C(10) | 5201(7)   | 3650(5)   | −1301(4) | 1069(12)  |
| C(11) | 3604(6)   | 2964(4)   | −143(4)  | 912(11)   |
| C(12) | −124(6)   | 1911(4)   | −1214(4) | 864(11)   |
| C(13) | −341(6)   | 2102(4)   | 1167(4)  | 793(10)   |
| C(14) | −2398(6)  | 1711(4)   | 1400(4)  | 814(11)   |
| C(15) | −3109(7)  | 550(5)    | 2645(4)  | 861(12)   |
| C(16) | −5198(7)  | 250(5)    | 2890(5)  | 890(13)   |
| C(17) | −5998(8)  | −966(6)   | 4067(5)  | 1018(16)  |
| C(18) | −8107(9)  | −1194(7)  | 4265(6)  | 1266(19)  |
| C(19) | −8949(11) | −2410(10) | 5365(7)  | 1183(27)  |
| C(20) | −10926(13)| −2646(12) | 5525(12) | 1891(39)  |

EXAMPLE 5

Rabbit Ear Perfusion Test

Female New Zealand White rabbits (approximately 4 kg) were anaesthetised with Sagatal ® (0.5 ml/kg).

The central ear artery was cannulated using a 20 G catheter and the ear cut off at its base. Heparinised (5 ml, 200 IU/ml) Krebs bicarbonate solution was perfused through the ear to expel the blood. The ear was placed in a warming jacket at 37° C. and attached via the arterial catheter to the perfusion pump. Perfusion of the ear with aerated (95% O$_2$/5% CO$_2$)Krebs bicarbonate solution at 37° C. was commended at a rate of 6.5 ml/min using a Watson Marlow peristaltic pump. The perfusion pressure was monitored continuously using a pressure transducer (Type 4-327-1221, Consolidated Electrodynamics) coupled to a Devices Recorder.

Following an equilibration period of 15 minutes, increased tone was induced in the preparation by addition of adrenaline (1 Lg/ml) to the perfusion fluid.

After a stable tone was observed, various concentrations of test compounds were injected into the perfusion fluid and examined for their effect on the perfusion pressure. The effect of vehicle (0.2 ml, 50% Krebs/50% ethanol) was also tested on the ear preparation.

The results on compounds 3 and 4 of the present invention obtained with the rabbit ear perfusion test are given in tables 3 and 4.

corded. Two different concentrations (M) were tested and compared with Nifedipine ($10^{-4}$M) which served as a reference drug.

Results:

TABLE 5

| TEST SAMPLE | % MUSCLE CONTRACTIONS |
|---|---|
| $\underline{4}$ ($10^{-4}$ M) | 55.0 |
| $\underline{4}$ ($10^{-5}$ M) | 78.0 |
| $\underline{D}$ ($10^{-4}$ M) | 95.7 |
| $\underline{D}$ ($10^{-5}$ M) | 101.6 |
| $\underline{F}$ ($10^{-4}$ M) | 46.9 |
| $\underline{F}$ ($10^{-5}$ M) | 60.7 |
| Acetylcholine ($3 \times 10^{-6}$ M) | 100.0 |
| Nifedipine ($10^{-4}$ M) | 0.0 |

TABLE 3

The effect of 3 on the isolated rabbit ear preparation.

|  | Tissue 1 | Tissue 2 |
|---|---|---|
| Mean % change in perfusion pressure for vehicle | 0 | −8,2% |

| Treatment | Dose (μ) | Tissue 1 *corrected % change in perfusion pressure | Tissue 2 corrected % change in perfusion pressure | Corrected mean % change in perfusion pressure | Mean time to return to pre-dose value (min) | ED$_{25}$ and 95% fiducial limits (μg) |
|---|---|---|---|---|---|---|
| $\underline{3}$ | 31.6 | −9.4 | 0 | −4.7 | 0 | |
|  | 100 | −7.7 | −20.5 | −14.1 | >4.0 | |
|  | 316 | −25.9 | −18.7 | −22.3 | >9.0 | 324 |
|  | 1000 | −24.0 | −56.6 | −40.3 | 13.0 | (230–438) |
|  | 3160 | −72.2 | −56.6 | −64.4 | 8.0 | |

*Perfusion pressure changes induced by $\underline{3}$ were corrected by subtracting values obtained with vehicle.

TABLE 4

A comparison of Compound 4 and Nifedipine on the isolated rabbit ear preparation.

|  | Tissue 1 | Tissue 2 | Tissue 3 |
|---|---|---|---|
| Mean % change in perfusion pressure for vehicle | 4.3 | 0 | 0 |

| Treatment | Dose (μg) | *Corrected % change in perfusion pressure Tissue 1 | Tissue 2 | Tissue 3 | Corrected % mean change in perfusion pressure | Mean time to return to pre-dose value (min) | ED$_{25}$ and 95% fiducial limits (μg) |
|---|---|---|---|---|---|---|---|
| $\underline{4}$ | 31.6 |  | −27.0 | −11.8 | −19.4 | >7.5 | 145 |
|  | 100 |  | −25.0 | −16.7 | −20.9 | 6.0 |  |
|  | 316 |  | −36.0 | −16.7 | −26.4 | >11.0 | 63–255 |
|  | 1000 |  | −36.4 | −44.4 | −40.4 | 8.0 |  |
|  | 3160 |  | −59.1 | −44.4 | −51.8 | 16.5 |  |
| Nifedi-pine | 31.6 | −22.7 |  | −30.0 | −26.4 | 4.0 |  |
|  | 100 | −18.7 |  | −22.7 | −20.7 | 4.5 | 111 |
|  | 316 | −28.0 |  | −22.7 | −25.4 | 5.0 |  |
|  | 1000 | −40.4 |  | −21.7 | −31.1 | >10.0 | <10–474 |
|  | 3160 | −40.7 |  | −33.7 | −37.2 | >9.5 |  |

Tone was induced in the rabbit ear by perfusion of Krebs bicarbonate solution containing 1 μg/ml adrenaline.
Values are a mean of two tissues.
− Indicates a reduction in perfusion pressure
*Corrected % change = drug effect - vehicle effect

EXAMPLE 6

Effect on Acetylcholine Induced Contractions in the Guinea Pig Ileum (in Vitro)

Experimental Procedure:

For statistical significance, three guinea pigs (Hartley Duncan strain) were used per test drug.

The ileal segment of a guinea pig was suspended in an organ bath containing a modified Krebbs solution at 37° C. The organ was coupled to an isotonic transducer and spontaneous contractions were recorded on a Harvard universal occilograph. Maximal contraction of the ileal segment was elicited by $3 \times 10^{-6}$M acetylcholine. The test drug was incubated into the organ bath and a reduction in the maximal response to acetylcholine was re-

EXAMPLE 7

Determination of Calcium Antagonist Activity on Depolarized Guinea Pig Ileum

Experimental Procedure:

To obtain results of statistical significance, three guinea pigs (Hartley Duncan strain) were used per test drug.

The ileal segment of a guinea pig was suspended in an organ bath containing a modified Krebbs solution at 37° C. The organ was coupled to an isotonic transducer and spontaneous contractions were recorded on a Harvard universal occilograph. The ileal segment was depolarized by changing the KCl concentration in the Krebbs solution to 100 mM. Contractile response to 3.0 mM $CaCl_2$ was recorded. The test drug was incubated in two different concentrations and inhibition of more than 80 percent (>80%) of the contractile response to 3.0 mM $CaCl_2$ indicates calcium antagonist activity.

Results:

TABLE 6

| TEST SAMPLE | % MUSCLE CONTRACTIONS |
| --- | --- |
| 4 ($10^{-4}$ M) | 18.8 |
| 4 ($10^{-5}$ M) | 86.3 |
| D ($10^{-4}$ M) | 162.5 |
| D ($10^{-5}$ M) | 119.7 |
| F ($10^{-4}$ M) | 59.4 |
| F ($10^{-5}$ M) | 96.2 |
| $CaCl_2$ (3 mM) | 100.0 |
| Nifedipine ($10^{-4}$ M) | 0.0 |

EXAMPLE 8

The Effect on Noradrenaline Induced Contractions in the Rat Aorta

Experimental Procedure:

For statistical significance, three rats (Sprague Dawley strain) were used per test drug.

An aortic tube segment of a rat was suspended in an organ bath containing a modified Krebbs solution at 37° C. The organ was coupled to an isotonic transducer and spontaneous contractions were recorded on a Harvard universal occilograph. Maximal contraction of the aorta tube was elicited by $3 \times 10^{-4}$M noradrenaline. The test drug was incubated into the organ bath and a reduction in the maximal response to noradrenaline was recorded. Two different concentrations (M) were tested and compared with Nifedipine ($10^{-4}$M) which served as a reference drug.

Results:

TABLE 7

| TEST SAMPLE | % MUSCLE CONTRACTIONS |
| --- | --- |
| 4 ($10^{-4}$ M) | 47.5 |
| 4 ($10^{-5}$ M) | 87.1 |
| D ($10^{-4}$ M) | 83.0 |
| D ($10^{-3}$ M) | 86.6 |
| F ($10^{-4}$M) | 66.1 |
| F ($10^{-5}$ M) | 88.1 |
| Noradrenaline ($3 \times 10^{-4}$ M) | 100.000 |
| Nifedipine ($10^{-4}$ M) | 41,570 |

In respect of pharmaceutical compositions, one or more of the above suitable compounds may be incorporated in a pharmaceutical composition for administration to a human or animal patient. The method of preparing such composition includes the steps of ensuring that the compound(s) are free of undesirable impurities this may require repeated re-crystllisation, or washing; comminuting the compound(s) to a required particle size; and incorporating and providing the compound(s) in a desired form together with a suitable adjuvant or diluent for administration to a patient for example in solid (powder, tablet or capsule form), or liquid form (injectable or liquid medicine) for internal application, for example in a suspension or cream, or in a (dissolved) jelly form.

Although the invention in its various aspects has been described above in certain preferred embodiments, it will be readily apparent to any person skilled in the art that various modifications and/or variations of the invention are possible. Such modifications and/or variations of the invention are to be considered as forming part of the invention and as falling within the scope of the invention as herein described.

We claim:

1. A 4-azahexacyclo dodecane compound of the formula:

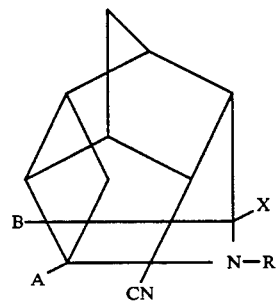

wherein

R, A and B each is hydrogen; a linear or branched alkyl group having one to twelve carbon atoms and optionally including a hydroxyl or halogen substituent; or a phenyl group alone or optionally substituted with a linear or branched alkyl group having one to twelve carbon atoms, which group optionally includes a hydroxyl or halogen substituent; and X is a hydroxyl or $-NR_2$ group where R is as stated above; or an acid addition salt of such compound.

2. The compound of claim 1 wherein X is a hydroxyl group; one of A and B is hydrogen; and R is $-CH_3$; $-(CH_2)_3-CH_3$; $-(CH_2)_7-CH_3$; $-CH_2-C_6H_5$; $-(CH_2)_2-C_6H_5$; $-(CH_2)_3-C_6H_5$; $-CH_2CH_3$; $-(CH_2)_{11}-CH_3$; $-CH_2CH(CH_3)_3$; $-(CH_2)_5-CH_3$; $-C(CH_3)_2-CH_2-C(CH_3)_3$; $-(CH_2)_9-CH_3$; $-CH_2-CH_2-OH$; or $-C_6H_5$.

3. The compound of claim 2 wherein one of A and B is hydrogen and the other is a methyl group.

4. The compound of claim 1 wherein X is $-NHR$ with R defined as above.

5. The compound of claim 4 wherein X is $-NHCH_2-C_6H_5$.

6. The compound of claim 4 wherein each R is $-CH_3$; $-(CH_2)_3-CH_3$; $-(CH_2)_7-CH_3$; $-CH_2-C_6H_5$; $-(CH_2)_2-C_6H_5$; $-(CH_2)_3-C_6H_5$; $-CH_2CH_3$; $-(CH_2)_{11}-CH_3$; $-CH_2CH(CH_3)$; $-(CH_2)_5-CH_3$; $-C(CH_3)_2-CH_2-C(CH_3)_3$; $-(CH_2)_9-CH_3$; $-CH_2-CH_2-OH$; or $-C_6H_5$.

7. The compound of claim 5 wherein R is $-CH_2-C_6H_5$.

8. The compound of claim 7 wherein at least one of A and B is hydrogen.

9. The compound of claim 7 wherein each of A and B is hydrogen.

10. A pharmaceutical composition comprising as an active ingredient, a therapeutically effective amount of a compound of one of claims 1-9 in combination with a diluent for administration of the composition to a patient.

11. The composition of claim 10 wherein the compound is present in an amount effective to be used as a calcium antagonist.

12. The composition of claim 10 wherein the compound is present in an amount effective to be used as a cardiac agent and an anti-hypertensive agent.

* * * * *